US00PP35987P2

(12) United States Plant Patent
Jan Kraan

(10) Patent No.: US PP35,987 P2
(45) Date of Patent: Jul. 9, 2024

(54) ***HYDRANGEA* PLANT NAMED 'BOKORUBS'**

(50) Latin Name: *Hydrangea paniculata*
Varietal Denomination: Bokorubs

(71) Applicant: Kees Jan Kraan, Alphen aan den Rijn (NL)

(72) Inventor: Kees Jan Kraan, Alphen aan den Rijn (NL)

(73) Assignees: BOOT & CO BOOMKWEKERIJEN BV, Boskoop (NL), part interest; KOLSTER BV, Boskoop (NL), part interest ( * ) Notice: Subject to any disclaimer, the term of this patent is extended or adjusted under 35 U.S.C. 154(b) by 304 days.

(21) Appl. No.: 17/977,040

(22) Filed: Oct. 31, 2022

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 5/00; A01H 6/48
See application file for complete search history.

(56) References Cited

U.S. PATENT DOCUMENTS

PP21,778 P2 * 3/2011 Kraan ..... A01H 6/48
Plt./250

* cited by examiner

*Primary Examiner* — June Hwu
(74) *Attorney, Agent, or Firm* — Penny J Aguirre

(57) ABSTRACT

A new cultivar of *Hydrangea macrophylla* plant named 'Bokorubs' that is characterized by its inflorescences with contrasting sterile flower sepals that are white in color when mature and age to dark pink in color, its medium sized compact plant habit, its inflorescences that are dense and conical-slightly ovate in shape, and its sturdy and healthy foliage that remains healthy during flowering.

2 Drawing Sheets

Botanical classification: *Hydrangea paniculata.*
Varietal denomination: 'Bokorubs'.

BACKGROUND OF THE INVENTION

The present invention relates to a new and distinct cultivar of *Hydrangea paniculata* and will be referred to hereafter by its cultivar name, 'Bokorubs'. 'Bokorubs' represents a new panicle *hydrangea*, a perennial shrub grown for landscape use.

'Bokorubs' derived from an ongoing controlled breeding program directed by the Inventor in Boskoop, The Netherlands. The goal of the breeding program included developing new cultivars of *Hydrangea paniculata* dense and compact plant habits, dense inflorescences, and more variations in the inflorescence shape.

'Bokorubs' originated as a seedling that arose from seed planted from open pollination of *Hydrangea* 'DVPPinky' (U.S. Plant Pat. No. 16,166) in August of 2011. 'Bokorubs' was selected as a single unique plant in August of 2021 from amongst the resulting seedlings.

Asexual propagation of the new cultivar was first accomplished by stem cuttings under the direction of the Inventors in August of 2016 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bokorubs' as a unique cultivar of *Hydrangea paniculata.*

1. 'Bokorubs' exhibits inflorescences with contrasting sterile flower sepals that are white in color when mature and age to dark pink in color.
2. 'Bokorubs' exhibits a medium sized compact plant habit.
3. 'Bokorubs' exhibits inflorescences that are dense and conical-slightly ovate in shape.
4. 'Bokorubs' exhibits sturdy and healthy foliage that remains healthy during flowering.

The seed parent of 'Bokorubs' differs from 'Bokorubs' in having a taller plant height, a more narrow and more upright plant habit, and inflorescences that are more conical in shape. 'Bokorubs' can be most closely compared to the *Hydrangea paniculata* cultivars 'Bokrathirteen' (U.S. Plant Pat. No. 21,778) and 'Bokraflame' (U.S. Plant Pat. No. 22,111). Both 'Bokrathirteen' and 'Bokraflame' are similar to 'Bokorubs' in plant habit. 'Bokrathirteen' differs from 'Bokorubs' in having foliage that is prone to leaf scorch (less healthy), inflorescences that are broadly ovate to slightly conical in shape, and sterile flower sepals that fade to light pink in color. 'Bokraflame' differs from 'Bokorubs' in having inflorescences that are broadly ovate to slightly conical in shape, and sterile flowers that cream colored at maturity and fade to dark pink-red in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listing by Plants Nouveau, Prides Corner, Overdevest, and Worry Free Plants.

BRIEF DESCRIPTION OF THE DRAWINGS

The accompanying color photographs illustrate the overall appearance and distinct characteristics of the new *Hydrangea*. The photographs were taken of a four-year-old plant of 'Bokorubs' as grown outdoors in a trial garden in Boskoop, The Netherlands.

The photograph in FIG. 1 provides a side view of the plant habit of 'Bokorubs' in bloom.

Figure 1:
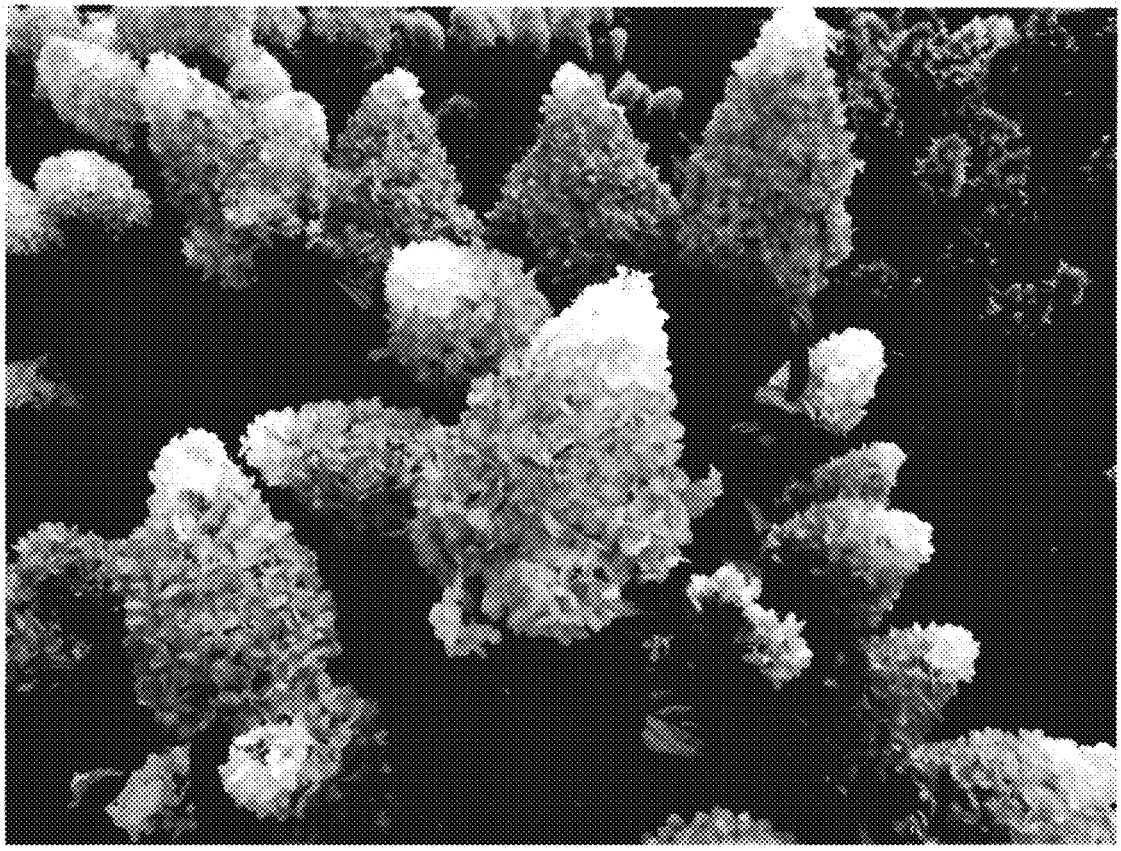
Figure 2:
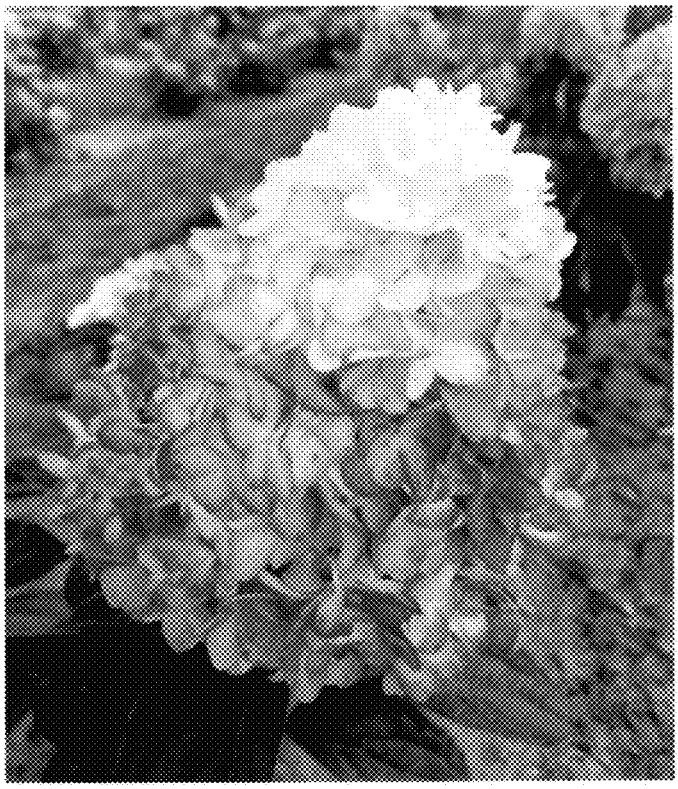

The photograph in FIG. 2 provides a close-up view of an aging inflorescence of 'Bokorubs'.

Figure 3:
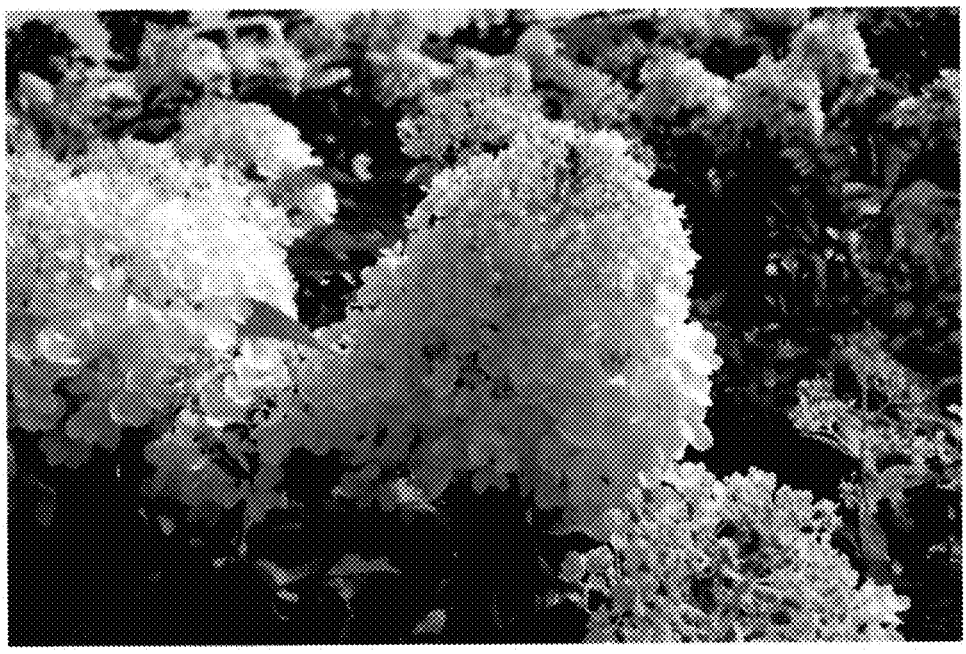

The photograph in FIG. 3 provides a close-up view of a mature inflorescence of 'Bokorubs'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of two-year-old plants of 'Bokorubs' as grown outdoors in the ground in a garden in West Newbury, Mass. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—July through September in Massachusetts.

*Plant type.*—Deciduous shrub, panicle type *Hydrangea.*

*Plant habit.*—Broadly upright, bushy and very compact.

*Height and spread.*—Reaches 92 cm in height and 122 cm in spread as a 2-year-old plant, reaches 1.5 m in height and 1 m in spread as a mature plant in the landscape.

*Hardiness.*—At least in U.S.D.A. Zones 4 to 9.

*Diseases and pests.*—No susceptibility and resistance to diseases or pests has been observed.

*Root description.*—Fine, fibrous and dense, NN155A and 164A in color.

*Propagation.*—Stem cuttings.

*Root development.*—6 to 8 weeks for root initiation with a finished plant produced in in a P9 container in about 12 months from a rooted cutting.

*Growth rate and vigor.*—Low to moderate.

Stem description:

*Stem shape.*—Rounded.

*Stem strength.*—Strong.

*Stem color.*—Young; 145A to 145B, mature; 199B to 199D, old bark; 197B and 199B.

*Stem size.*—Average of 55 cm in length (excluding inflorescence) and 4 mm in diameter.

*Stem surface.*—Young stems are matte and densely covered with short stiff hairs; an average of 0.5 mm in length that match surface color, mature stems are matte and moderately covered with lenticels; an average of 1.5 mm in length and 0.75 mm in width, 199D in color, mature bark is mostly smooth and lacks fasciation.

*Stem aspect.*—Upright, average of 55° to soil level, varying between 20° and 90°.

*Internode length.*—An average of 7 cm.

*Branching.*—Freely branching with an average of 16 branches from base.

Foliage description:

*Leaf shape.*—Ovate to narrow ovate.

*Leaf arrangement.*—Opposite or in whorls of three.

*Leaf division.*—Simple.

*Leaf base.*—Obtuse to short attenuate.

*Leaf apex.*—Apiculate.

*Leaf margins.*—Serrate.

*Leaf venation.*—Pinnate, color; upper surface 144B, lower surface 145C.

*Leaf size.*—An average of 9 cm in length and 5 cm in width.

*Leaf attachment.*—Petiolate.

*Leaf number.*—An average of 24 per lateral stem.

*Leaf surface.*—Both surfaces; smooth and very slightly rugose, both surfaces sparsely to moderately covered with short adpressed strigose hairs; average of 0.3 mm in length, 157D in color.

*Leaf color.*—Young upper surface; NN137D, young lower surface 146B, mature upper surface; between NN137B, mature lower surface; 147B, fall color is non-showy and about 137C in color on the upper surface and 147D on the lower surface.

*Petioles.*—An average of 2 cm in length and 2.5 mm in diameter, upper surface color N144D, proximal end N144C, lower surface color 144D, proximal end 144C, both surfaces matte and sparsely covered with very short hairs an average of 0.3 mm in length and too small to measure color.

Inflorescence description:

*Inflorescence type.*—Terminal conical-slightly ovate shaped panicle, comprised of sterile flowers above inconspicuous fertile flowers that are broadly conical to nearly globose in shape.

*Lastingness of inflorescence.*—Sterile flowers; persistent for an average of 6 weeks, fertile flowers; never open but persist.

*Inflorescence number.*—One per lateral stem.

*Inflorescence size.*—An average of 15 cm in height and 6 cm in diameter.

*Flower number.*—An average of 450 sterile flowers and 200 fertile flowers per panicle.

*Flower fragrance.*—None.

*Flower aspect.*—Sterile flowers; held upright to outward and slightly drooping, fertile flowers; held upright from peduncle.

*Flower size.*—Sterile flowers; up to 3 cm in diameter and 0.7 mm in depth, fertile flowers; an average of 1.3 cm in diameter and 7 mm in depth.

*Flower type.*—Sterile flowers rotate, fertile flowers rotate and dropped when mature.

*Flower buds.*—Sterile flowers; an average of 0.5 mm in length and 1.3 cm in diameter, broadly cup-shaped, between 145B and 150D in color, fertile flowers; an average of 3 mm in length, 2 mm in diameter, obovate in shape, color; 145D, immature calyx 193A.

*Petals.*—Sterile flowers; 4, 3.5 mm in length and 1.5 mm in width, glabrous, matte surfaces, upper and lower surface color 155A, fertile flowers; 5, rotate and cruciform in shape, ovate to concave in shape, acute apex, cuneate base, entire margins, average of 4 mm in length and 2.5 mm in width, upper surface glabrous and slightly glossy, lower surface glabrous and matte, color; when opening and fully open upper and lower surface 145C.

*Peduncles.*—Primary peduncles; strong, flattened oval in shape, an average of 3 cm in length and 2 mm in width. secondary peduncles 2 cm in length and 2 mm in width, 157A in color, surface is matte and moderately covered with thin pubescence; hairs an average of 0.3 mm in length and 145D in color.

*Pedicels.*—Sterile flowers; moderate strength, an average of 1.6 cm in length and 1 mm in width, color; 157D, proximal end 157A, held at a 45° angle, surface is matte and moderately covered with thin pubescence an average of 0.3 mm in length and 157D in color, fertile flowers; moderate strength, an average of 3 mm in length, 0.5 mm in diameter, held at a 30° angle, 145D in color, surface is matte and densely covered with thin pubescence; hairs an average of 0.3 mm in length and 145D in color.

*Sepals.*—Sterile flowers; 4 (occasionally 3 or 5), rotate, ovate to obovate, slightly carinate in shape, very weakly overlapping, obtuse apex, cuneate base, entire margins, average of 1.4 cm in length and 1.2 cm in width, both surfaces; glabrous and matte, color; upper surface when opening 155C, lower surface when opening N155A, upper and lower surface when fully open N155A, fading to 144D, then finally 185C, fertile flowers; 5, rotate, broadly deltoid in shape, broad acuminate apex, broad cuneate base, entire margins, 1 mm in length, 1.5 mm in width, both surfaces glabrous and matte, color; when opening upper surface 144D, when opening lower surface 193A, when fully open upper surface and lower surface 144C.

*Bracts.*—None observed.

Reproductive organs:

*Gynoecium.*—Sterile flowers; none observed, fertile flowers; none observed as flowers never open.

*Androecium.*—Sterile flowers; none observed, fertile flowers; none observed as flowers never open.

*Fruit and seed.*—None observed to date.

It is claimed:

1. A new and distinct cultivar of *Hydrangea* plant named 'Bokorubs' substantially as herein illustrated and described.

* * * * *